United States Patent [19]

Bitterli et al.

[11] Patent Number: 5,021,573

[45] Date of Patent: Jun. 4, 1991

[54] HETEROCYCLIC PIGMENTS AND DYES

[75] Inventor: Peter Bitterli, Reinach, Switzerland; Bansi L. Kaul, Biel-Benken, both of Switzerland

[73] Assignee: Sandoz Ltd., Basel, Switzerland

[21] Appl. No.: 340,348

[22] Filed: Apr. 19, 1989

[30] Foreign Application Priority Data

Apr. 20, 1988 [DE] Fed. Rep. of Germany ....... 3813243

[51] Int. Cl.$^5$ .................. C07D 403/14; C07D 487/02; C07D 417/00; C07D 235/04
[52] U.S. Cl. ..................................... 544/284; 548/156; 548/159; 548/181; 548/327; 548/328; 548/336; 548/374; 548/433
[58] Field of Search ............... 544/284; 548/156, 159, 548/181, 327, 328, 336, 374, 433

[56] References Cited

U.S. PATENT DOCUMENTS

| 4,255,313 | 3/1981 | Antonoplos et al. | 548/433 |
| 4,289,784 | 9/1981 | Bochis et al. | 548/433 |
| 4,320,129 | 3/1982 | Fisher et al. | 548/433 |

FOREIGN PATENT DOCUMENTS

| 2236629 | 2/1973 | Fed. Rep. of Germany. | |
| 48-30656 | 9/1973 | Japan | 544/284 |
| 49-28650 | 7/1974 | Japan | 544/284 |
| 2108862 | 5/1987 | Japan | 548/433 |
| 1561122 | 2/1980 | United Kingdom. | |
| 1601267 | 10/1981 | United Kingdom. | |

OTHER PUBLICATIONS

Hodd, Chem. Abst., 78-137959z, (1973).
Diebig et al., Chem. Abst., 80-3827n, (1974).
Hodd et al., Chem. Abst., 87-6400y, (1977).
Chem. Abs., 100:192426w, (1984).
Chem. Abs., 88:145368c.
Chem. Abs., 73:131375f, (1970).

Primary Examiner—Cecilia Shen
Attorney, Agent, or Firm—Gerald D. Sharkin; Richard E. Vila; Thomas C. Doyle

[57] ABSTRACT

A compound of formula I

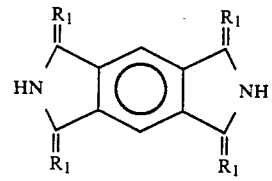

in which each $R_1$ independently is selected from oxygen, $=NH$ or $=N-R_2$ where $R_2$ is an aromatic or heteroaromatic group, provided not more than two groups $R_1$ are selected from oxygen and $=NH$.

12 Claims, No Drawings

HETEROCYCLIC PIGMENTS AND DYES

The invention relates primarily to pigments or solvent dyes, suitable for pigmenting or dyeing plastics in the mass.

According to the invention, there is provided a compound of formula I

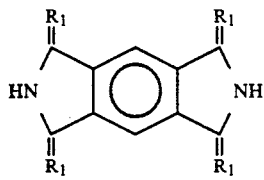
(I)

in which each $R_1$ independently is selected from oxygen, $=NH$ or $=N-R_2$ where $R_2$ is an aromatic or heteroaromatic group, provided not more than two groups $R_1$ are selected from oxygen and $=NH$.

Preferably when $R_2$ is an aromatic group, it is a group of formula α or β

(α)

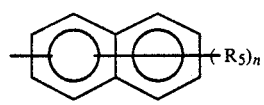
(β)

where
n is 0, 1, 2 or 3 and
each $R_5$ independently is selected from halogen, ($C_{1-4}$ alkyl)aminocarbonyl, ($C_{1-4}$ alkyl)carbonylamino, carboxyl, ($C_{1-4}$ alkoxy)carbonyl, phenlaminocarbonyl, benzoylamino or phenyloxycarbonyl or $R_5$ is a group of formula δ

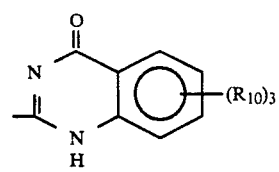
(δ)

where each $R_{10}$ independently is hydrogen, halogen, $C_{1-4}$ alkyl, $C_{1-4}$ alkoxy, cyan or nitro; provided not more than one group $R_5$ attached to any one phenyl group is a group of formula δ.

Preferably each $R_{10}$ is hydrogen.

Preferably when $R_2$ is a heteroaromatic group, it is a thienyl, thiazolyl, pyrazolyl, imidazolyl, benzthiazolyl or benzimidazolyl group.

Preferably $R_1$ is $R_1'$ where each $R_1'$ independently is selected from oxygen, $=NH$ and $=N-R_2$ where $R_2$ is a group of formula α, provided that not more than two groups $R_1'$ in the compound of formula I are selected from oxygen and $=NH$.

More preferably $R_1$ is $R_1''$ where each group $R_1''$ independently is $=N-R_2'$ where $R_2'$ is a group of formula α'

(α')

where
N' is 2 or 3; and
each $R_5'$ independently is chloro, bromo, ($C_{1-4}$ alkyl)aminocarbonyl, ($C_{1-4}$ alkyl)carbonylamino, carboxyl, ($C_{1-4}$ alkoxy)carbonyl, phenylaminocarbonyl, benzoylamino, phenoxycarbonyl or a group of formula δ'

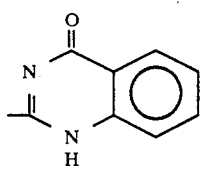
(δ')

provided that not more than one group $R_5'$ attached to any one phenyl group is a group of the formula δ'.

Most preferably $R_1$ is $R_1'''$ where each group $R_1'''$ independently is $=N-R_2''$ where $R_2''$ is a group of the formula α''

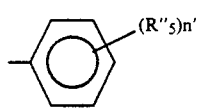
(α'')

where
n' is 2 or 3; and
each $R_5''$ independently is benzoylamino, chloro or bromo.

Especially preferred $R_1'''$ is $R_1^{IV}$ where each $R_1^{IV}$ independently is $=N-R_2'''$ where $R_2'''$ is a group of formula α''', $α^{IV}$ and $α^V$

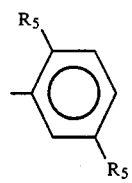
(α''')

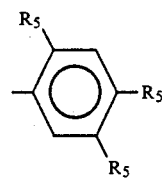
($α^{IV}$)

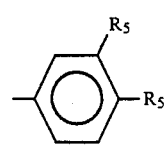
($α^V$)

where each $R_{10}$ independently is selected from Br and Cl.

Preferred groups of $R_2'''$ are of formula $α^{VI}$–$α^{VIII}$

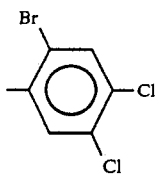
(α^{VI})

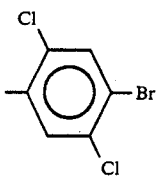
(α^{VII})

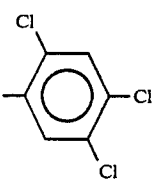
(α^{VIII})

Compounds of formula I can be prepared by reacting one mole of the compound of formula II

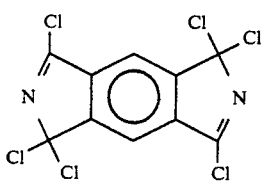
(II)

with (a) four moles of a compound of formula III $$R_1-NH_2$$ (III)

or (b) three moles of a compound of formula III and one mole of water or ammonia; or (c) two moles of a compound of formula III and two moles of water or ammonia or one mole of water and one mole of ammonia.

The compounds of formula II and III are known or may be made from known compounds by known methods.

The reaction of the compound of formula II with a compound of formula III can take place at an elevated temperature, preferably from 80°-120° C. according to known methods.

The compounds of formula I are useful for dyeing in the mass plastics material. By the term "dyeing in the mass" is meant dyeing in solvent-containing masses, dyeing in solvent free masses and dyeing in plastics resins, by known methods.

Such processes include colouring oil based or water based paints or lacquers, spin dyeing from viscose or cellulose acetate, pigmenting of polyethylene, polystyrene, polyvinylchloride, rubber and artifical leather.

The compounds of formula I can also be used for print dyeing of graphic fabrics, for dyeing paper masses, for coating textiles or for pigments printing.

Compounds of formula I where $R_1$ is $=N-R_2$ where $R_2$ is a group of formula α, n'=2 or 3 of and where $R_5$ is $R_5''$ are pigments. The remaining compounds are suitable for mass dyeing of polyester melts in which they tend to form a homogeneous solution.

The dyeings, especially the pigment dyeings, have good heat fastness, good light fastness, good weather fastness, good fastness to chemicals, good migration fastness, good fastness to blooming, good fastness to overcoating, good fastness to solvents. The dyeing strength is good and the compounds have good application properties, for instance good flocculation ability, good crystallinity and good dispersability.

The invention will now be illustrated by the following Examples in which all temperatures are in ° C.

EXAMPLE 1

18.15 g of the compound of formula II

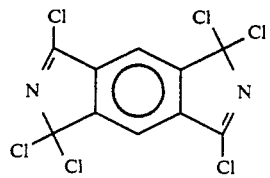
(II)

are dispersed in 100 mls of ortho dichlorobenzene whilst stirring at 120° C. The dispersion is cooled to 100° C. and mixed with 49.0 g of 2,4,5 trichloroaniline in 150 mls of ortho dichlorobenzene. The resulting mixture is heated to 110° C. and stirred at this temperature for 12 hours. The resulting pigment is of formula 1a

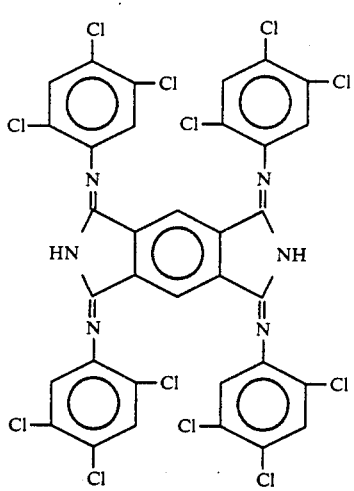
(1a)

The pigment of formula 1a is filtered hot and then washed with ortho dichlorobenzene, methanol and finally water.

(a) The pigment can be used as such without any further treatment for dyeing or pigmenting of plastics and lacquers. By incorporating the pigment into a clear lacquer containing pigment and $TiO_2$ in a ratio of 1:10, a reddish yellow colouring of the lacquer is produced with good fastness properties. Such a dyeing has a colorimetric value of H*(Hue)=60.27, C*(Chroma)=52.12, and L*(Lightness)=77.69.

(b) The pigment may, instead of being used directly, be recrystallised in dimethylformamide and a β modification is formed having an X ray pattern significantly different to the α-form. The β modification can also be used to dye or pigment directly in plastics and lacquers. When the pigment is added to a clear commercially available alkyl-melamine-formaldehyde a yellowish colouring is imparted to the lacquer with good fastness properties. The Colorimetric Values in a clear lacquer containing pigment and TiO$_2$ in a 1:10 ratio is H*=70.82, C*=63.66 and L*=82.06.

The X-ray data for the α-modification is: 5.6(w); 4.18(w); 3.99(w); 3.81(w); 3.57(w); 3.53(w); 3.45(w); 3.34(w); 3.22(w); 2.94(w).

The X-ray data for the β-modification is: 10.6(w); 6.5(w); 6.2(w); 5.8(w); 4.4(w); 3.5(w); 3.35(w); 3.11(w). in which w is weak.

EXAMPLES 2 to 10

Compounds of the formula I

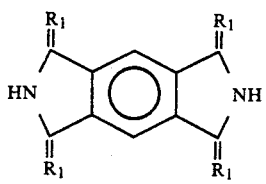
(I)

where R$_1$ is defined in the Table below can be prepared from appropriate reactant according to the method of Example 1.

| Ex. | R$_1$ | Nuance of Dyeing | Colorimetric H* | C* | L* |
|---|---|---|---|---|---|
| 2 | 2,5-dichloro-4-benzoylamino-phenylimino | orange | 43.73 | 50.90 | 67.45 |
| 3 | 2,5-dichlorophenylimino | yellow | 76.60 | 50.59 | 86.19 |
| 4 | 3,4-dibromophenylimino | brownish-yellow | 74.34 | 42.97 | 70.10 |
| 5 | 2,5-dibromophenylimino | yellow | 80.40 | 56.22 | 85.60 |
| 6 | 2,5-dichloro-4-bromophenylimino | reddish-yellow | 59.31 | 52.39 | 76.60 |
| 7 | 2-bromo-4,5-dichlorophenylimino | reddish-yellow | 63.94 | 58.22 | 79.05 |
| 8 | 2,4-dibromophenylimino | yellow | 70.83 | 58.11 | 81.46 |
| 9 | 2,4-dichlorophenylimino | yellow | — | — | — |
| 10 | 2,5-dichloro-4-acetylamino-phenylimino | brown yellow | — | — | — |

APPLICATION EXAMPLE 4 g of the β modification of Example 1 and 40 g of titanium dioxide pigment are milled in a ball mill for 24 hours with 96 g of a mixture of
50 g of a 60% solution of coco-aldehyde-melamine resin (with 32% fatty content) in xylene;
30 g of a 50% melamine resin solution in butan-1-ol;
10 g of xylene; and
6 g of ethylene glycolmonoethyl ether.

The resulting dispersion is sprayed on an aluminium piece, air dried for 30 minutes and stored for 30 minutes at 120° C. A brilliant yellow film results with good light and weathering fastnesses.

The Application Example can be repeated using, instead of 4 g of β modification of Example, 4 g of any one of the products of Examples 2 to 10 or of the α modification of Example 1.

What is claimed is:

1. A compound of formula I

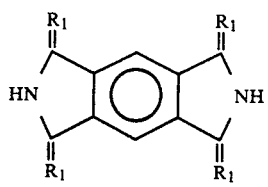
(I)

in which each R$_1$, independently, is oxygen, =NH or =N—R$_2$ where R$_2$ is a thienyl, pyrazolyl, imidazolyl, benzthiazolyl or benzimidazolyl group or a group of formula α or β

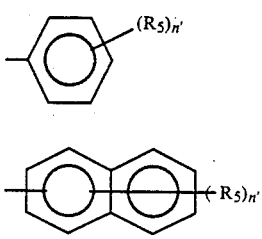
(α)

(β)

where n' is 2 or 3 and each R$_5$, independently, is halogen, (C$_{1-4}$ alkyl)aminocarbonyl, (C$_{1-4}$ alkyl)carbonylamino, carboxyl, (C$_{1-4}$ alkoxy)carbonyl, phenylaminocarbonyl, benzoylamino, phenoxycarbonyl or a group of formula δ

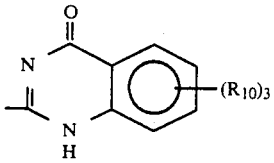
(δ)

where each R$_{10}$, independently, is hydrogen, halogen, C$_{1-4}$ alkyl, C$_{1-4}$ alkoxy, cyano or nitro, provided not more than one group R$_5$ attached to any one phenyl group is a group of formula δ; provided that not more than two groups R$_1$ are selected from oxygen and =NH.

2. A compound of formula I'

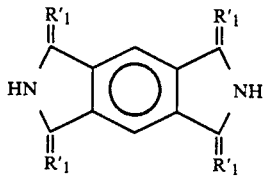
(I')

in which each R'$_1$, independently, is oxygen, =NH or =N—R$_2$ where R$_2$ is a group of formula α

(α)

where n' is 2 or 3 and each R$_5$, independently, is halogen, (C$_{1-4}$ alkyl)aminocarbonyl, (C$_{1-4}$ alkyl)carbonylamino, carboxyl, (C$_{1-4}$ alkoxy)carbonyl, phenylaminocarbonyl, benzoylamino, phenoxycarbonyl or a group of formula δ

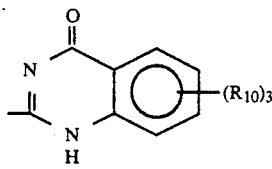 (δ)

where each $R_{10}$, independently, is hydrogen, halogen, $C_{1-4}$ alkyl, $C_{1-4}$ alkoxy, cyano or nitro; provided not more than one group $R_5$ attached to any one phenyl group is a group of formula δ; provided that not more than two groups $R'_1$ are selected from oxygen and —NH.

3. A compound according to claim 2 in which $R_1'$ is $R_1''$ where each group $R_1''$ independently is =N—$R_2'$ where $R_2'$ is a group of formula α'

 (α')

where
n' is 2 or 3 and
each $R'_5$ independently is selected from chloro, bromo, ($C_{1-4}$ alkyl)aminocarbonyl, ($C_{1-4}$ alkyl)carbonylamino, carbonyl, ($C_{1-4}$ alkoxy)carbonyl, phenylaminocarbonyl, benzoylamino, phenoxycarbonyl or a group of formula δ'

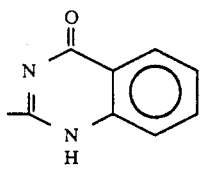 (δ')

provided that not more than one group $R_5'$ attached to any one phenyl group is a group of formula δ'.

4. A compound according to claim 2 in which $R_1'$ is $R_1'''$ where each group $R_1'''$ independently is =N—$R_2''$ where $R_2''$ is a group of formula α"

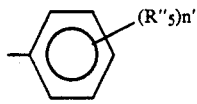 (α")

where
n' is 2 or 3; and
each $R_5''$ independently is benzoylamino, chloro or bromo.

5. A compound according to claim 2 in which $R_1'$ is $R_1^{IV}$ where each $R_1^{IV}$ independently is =N—$R_2'''$ where $R_2'''$ is a group of formula α''' to $α^V$

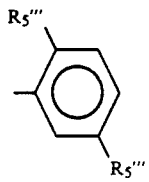 (α''')

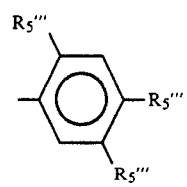 ($α^{IV}$)

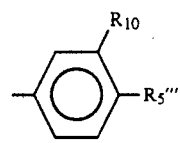 ($α^V$)

where each $R_{10}$ independently is chloro or bromo.

6. A compound according to claim 1 of formula I in which $R_1$ is =N—$R_2$ where $R_2'''$ is a group of the formula $α^{VI}$ to $α^{VIII}$

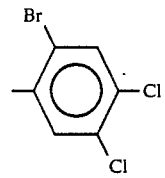 ($α^{VI}$)

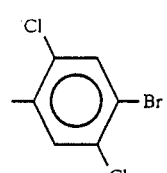 ($α^{VII}$)

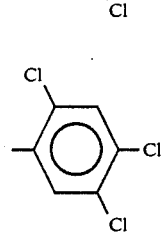 ($α^{VIII}$)

7. A compound according to claim 1 wherein each $R_{10}$ is hydrogen.

8. A compound according to claim 2 wherein each $R_{10}$ is hydrogen.

9. A compound according to claim 2 wherein each group $R_1'$ is the same and is selected from the group consisting of 2,4,5-trichlorophenylimino, 2,5-dichloro-4-benzoylaminophenylimino, 2,5-dichlorophenylimino, 3,4-dibromophenylimino, 2,5-dibromophenylimino, 2,5-dichloro-4-bromophenylimino, 2-bromo-4, 5-dichlorophenylimino, 2,4-dibromophenylimino, 2,4-dichlorophenylimino and 2,5-dichloro-4-acetylaminophenylimino.

10. The compound according to claim 7 of the formula

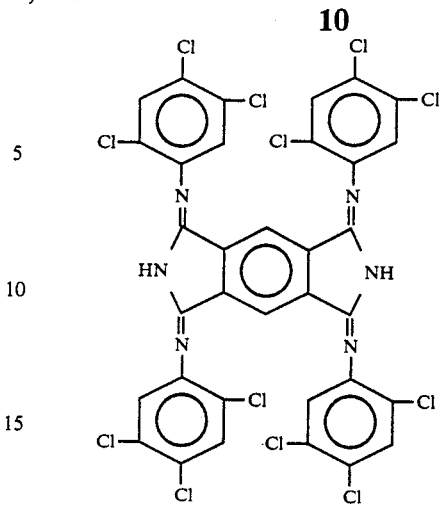
11. The α-modification of the compound of claim 8 having the following X-ray data: 5.6(w), 4.18(w), 3.99(w), 3.8'(w), 3.57(w), 3.53(w), 3.45(w), 3.34(w), 3.22(w), 3.22(w), 2.94(w), in which w is weak.
12. The β-modification of the compound of claim 8 having the following X-ray data: 10.0(w), 6.5(w), 6.2(w), 5.8(w), 4.4(w), 3.5(w), 3.35(w), 3.11(w), in which w is weak.
* * * * *